United States Patent [19]

Drabek et al.

[11] 4,264,624
[45] Apr. 28, 1981

[54] PESTICIDAL 3-PHENOXYBENZYL α-CYCLOPROPYL α-PHENYL-ACETATES

[75] Inventors: Jozef Drabek, Oberwil; Peter Ackermann, Reinach; Saleem Farooq, Ettingen; Laurenz Gsell, Basel; Odd Kristiansen, Möhlin; Rudolf Wehrli, Rheinfelden, all of Switzerland

[73] Assignee: Ciba-Geigy Corporation, Ardsley, N.Y.

[21] Appl. No.: 49,365

[22] Filed: Jun. 18, 1979

[30] Foreign Application Priority Data

Jun. 26, 1978 [CH] Switzerland .......................... 6937/78
Dec. 19, 1978 [CH] Switzerland ........................ 12885/78
Apr. 12, 1979 [CH] Switzerland .......................... 3532/79

[51] Int. Cl.³ .................. A01N 37/10; A01N 37/34; C07C 69/612; C07C 121/75
[52] U.S. Cl. .................. 424/304; 260/465 D; 424/308; 560/101
[58] Field of Search .................. 260/465 D; 560/101; 424/304, 308

[56] References Cited

U.S. PATENT DOCUMENTS 3,973,036 8/1976 Hirano et al. .......................... 424/304
4,137,324 1/1979 Elliott et al. ...................... 424/304 X

*Primary Examiner*—Dolph H. Torrence
*Attorney, Agent, or Firm*—Frederick H. Rabin

[57] ABSTRACT

α-Phenyl-α-cyclopropylacetates of the formula

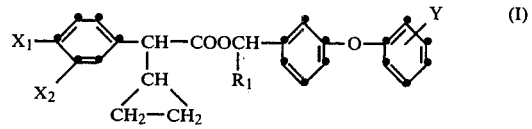

wherein $X_1$ represents hydrogen, halogen or $C_1$–$C_4$ alkyl, $X_2$ represents hydrogen, methyl or halogen, $R_1$ represents hydrogen, cyano, vinyl or ethynyl, and Y represents fluorine or bromine, processes for their manufacture, and a method of controlling pests which comprises the use of these novel esters.

5 Claims, No Drawings

PESTICIDAL 3-PHENOXYBENZYL α-CYCLOPROPYL α-PHENYL-ACETATES

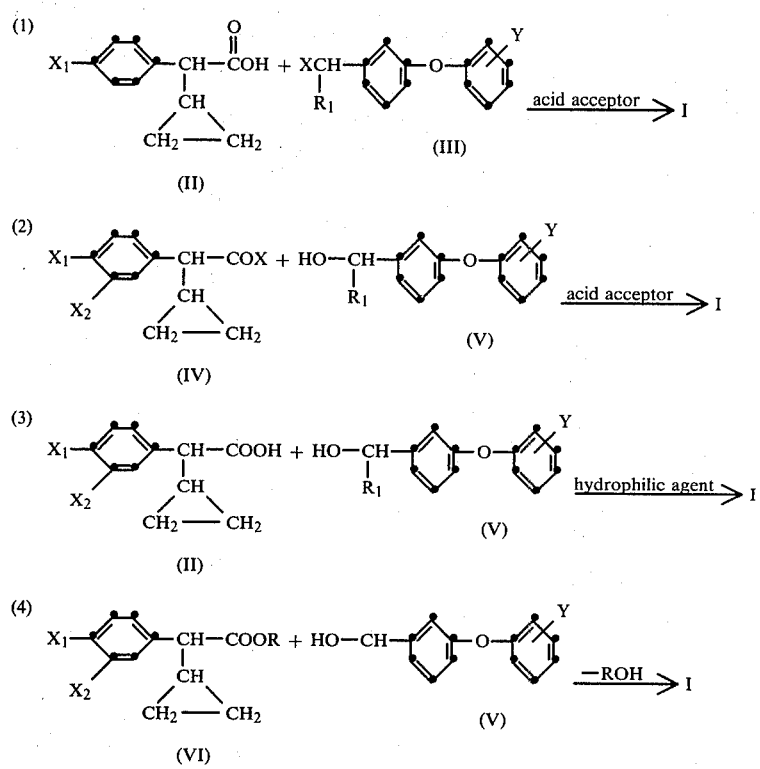

The present invention relates to α-phenyl-α-cyclopropylacetates, processes for their manufacture, and a method of controlling pests which comprises the use of these novel esters.

The α-phenyl-α-cyclopropylacetates have the formula

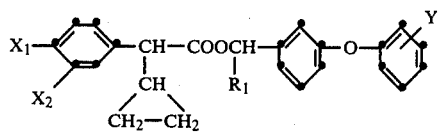

wherein $X_1$ represents hydrogen, halogen or $C_1$-$C_4$alkyl, $X_2$ represents hydrogen, methyl or halogen, $R_1$ represents hydrogen, cyano, vinyl or ethynyl, and Y represents fluorine or bromine.

By halogen is meant in this connection fluorine, chlorine, bromine or iodine, but especially chlorine.

Possible alkyl groups $X_1$ are for example: methyl, ethyl, propyl, isopropyl, n-butyl, isobutyl, sec-butyl, tert-butyl. Preferred compounds on account of their action are those of the formula I, wherein $X_1$ represents hydrogen, chlorine or methyl, $X_2$ represents hydrogen or chlorine, $R_1$ represents hydrogen, cyano, vinyl or ethynyl, and Y represents fluorine or bromine.

The most preferred compounds, however, are those of the formula I, wherein $X_1$ represents chlorine or methyl, $X_2$ represents hydrogen, $R_1$ represents cyano or ethynyl, and Y represents o-fluorine, m-fluorine or p-fluorine.

The compounds of the formula I can be obtained by methods which are known per se, for example as follows:

In the formulae II to VI, $X_1$, $X_2$, Y and $R_1$ are as defined for formula I.

In the formulae III and IV, X represents a halogen atom, especially a chlorine or bromine atom, and in formula VI R represents $C_1$-$C_4$alkyl, especially methyl or ethyl.

Suitable acid acceptors for processes 1 and 2 are in particular tertiary amines, such as trialkylamine and pyridine, and also hydroxides, oxides, carbonates and bicarbonates of alkali metals and alkaline earth metals, and in addition alkali metal alcoholates, for example potassium tert-butylate and sodium methylate. As hydrophilic agent for process 3, dicyclohexylcarbodiimide can be used for example. Processes 1 to 4 are carried out at a reaction temperature between $-10°$ and $120°$ C., usually between $20°$ and $80°$ C., under normal or elevated pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxamides; aliphatic, aromatic and halogenated hydrocarbons, especially benzene, toluene, xylenes, chloroform and chlorobenzene; nitriles, such as acetonitrile; dimethyl sulfoxide; and ketones, such as acetone and methyl ethyl ketone.

The starting materials of the formulae II to VII are known or they can be prepared by methods analogous to known ones.

The compounds of the formula I are in the form of a mixture of different optically active isomers if individual optically active starting materials are not used in the reaction. The different isomer mixtures can be separated into the individual isomers by known methods. The compound of the formula I is to be understood as comprising both the individual isomers and the mixtures thereof. The compounds of the formula I are suitable for controlling a variety of animal and plant pests. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocotera and Hymenoptera.

In particular, the compounds of the formula I are suitable for controlling insects which are harmful to plants, especially insects which damage plants by eating, in ornamentals and crops of useful plants, especially in cotton plantations (e.g. Spodoptera littoralis and Heliothis virescens) and in vegetable crops (for example Leptinotarsa decemlineata and Myzus persicae).

The active compounds of the formula I also have a very good action against flies, for example Musca domestica and mosquito larvae.

Surprisingly, the compounds of the formula I have a broader insecticidal activity spectrum than chemically analogous compounds disclosed in German Offenlegungsschrift 2 717 414.

The acaricidal and/or insecticidal action can be substantially broadened and adapted to prevailing circumstances by addition of other insecticides and/or acaricides. Examples of suitable additives include: organic phosphorus compounds, nitrophenols and derivatives thereof, formamidines, ureas, pyethroids, carbamates, and chlorinated hydrocarbons.

Compounds of the formula I are also combined with particular advantage with substances which exert a synergistic or potentiating effect on pyrethroids. Examples of such compounds include: piperonyl butoxide, propynyl ether, propynyl oximes, propynyl carbamates and propynyl phosphates, 2-(3,4-methylenedioxyphenoxy)-3,6,9-trioxaundecane (Sesamex or Sesoxane), S,S,S-tributylphosphorotrithioate, 1,2-methylenedioxy-4(2-(octylsulfinyl)-propyl)-benzene.

The compounds of the formula I may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners, binders and/or fertilisers.

The compositions of the present invention are manufactured in known manner by homogeneously mixing and/or grinding active substances of the formula I with the suitable carriers, with or without the addition of dispersants or solvents which are inert to the active substances.

The compounds of the formula I may be processed to the following formulations:
Solid formulations:
Dusts, tracking powders and granules (coated granules, impregnated granules and homogeneous granules).
Liquid formulations:
(a) active substances which are dispersable in water: wettable powders, pastes and emulsions;
(b) solutions.

The content of active substance in the above described compositions is generally between 0.1% and 95%, though concentrations of up to 99.5% or even pure active substance can also be used if the compositions are applied from an aircraft or other appropriate application devices.

The compounds (active substances) of the formula I can, for example, be formulated as follows (throughout the present specification all parts and percentages are by weight):

DUSTS

The following substances are used to formulate (a) a 5% and (b) a 2% dust:

(a)

5 parts of active substance,
95 parts of talc;

(b)

2 parts of active substance,
1 part of highly disperse silicic acid,
97 parts of talc.

The active substance is mixed with the carriers and ground.

GRANULES

The following substances are used to formulate 5% granules:
5 parts of active substance
0.25 parts of epichlorohydrin,
0.25 parts of cetyl polyglycol ether,
3.50 parts of polyethylene glycol,
91 parts of kaolin (particle size 0.3 –0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDERS:

The following constituents are used to formulate (a) a 40%, (b) and (c) a 25%, and (d) a 10% wettable powder:
(a)
40 parts of active substance,
5 parts of sodium dibutylnaphthalenesulfonate,
54 parts of silicic acid.

(b)

25 parts of active substance,
4.5 parts of calcium ligninsulfonate,
1.9 parts of Champagne chalk/hydroxyethyl cellulose mixture (1:1),
1.5 parts of sodium dibutylnaphthalenesulfonate,
19.1 parts of silicic acid,
19.5 parts of Champagne chalk,
28.1 parts of kaolin, (c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance, 3 parts of a mixture of the sodium salts of saturated fatty alcohol sulfates,
5 parts of naphthalenesulphonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

EMULSIFIABLE CONCENTRATES:

The following substances are used to formulate (a) a 10%, (b) a 25% and (c) a 50% emulsifiable concentrate:

(a)
10 parts of active substance,
3.4 parts of epoxidised vegetable oil,
3.4 parts of a combination emulsifier consisting of fatty alcohol polyglycol ether and alkylarylsulfonates calcium salt,
40 parts of dimethyl formamide,
43.2 parts of xylene;

(b)
25 parts of active substance,
2.5 parts of epoxidised vegetable oil,
10 parts of alkylarylsulfonate/fatty alcohol polyglycol ether mixture,
5 parts of dimethyl formamide,
57.5 parts of xylene;

(c)
50 parts of active substance,
4.2 parts of tributylphenol-polyglycol ether,
5.8 parts of cylcium dodecylbenzenesulfonate,
20 parts of cyclohexanene,
20 parts of xylene.

By diluting these concentrates with water it is possible to obtain emulsions of the required concentration.

SPRAYS:

The following ingredients are used to formulate (a) a 5% spray, and (b) a 95% spray:

(a)
5 parts of active substance,
1 part of epichlorohydrin,
94 parts of ligroin (boiling range 160°–190° C.);

(b)
95 parts of active substance,
5 parts of epichlorohydrin.

The invention is further illustrated by the following Examples.

EXAMPLE 1

Manufacture of (3-(4-fluorophenoxy)-α-cyanobenzyl α-cyclopropyl-4-chlorophenylacetate With stirring, 1 g of pyridine in 3 ml of toluene and 2.3 g of α-cyclopropyl-4-chlorophenylacetyl chloride in 3 ml of toluene are added successively at 0° to 10° C. to a solution of 2.43 g of 3-(4-fluorophenoxy)-α-cyanobenzyl alcohol in 20 ml of toluene. After stirring for 10 hours at room temperature, the reaction mixture is washed with water, 2 N hydrochloric acid and 3% sodium bicarbonate solution. The organic layer is dried over sodium sulfate and the toluene is distilled off, affording the compound of the formula

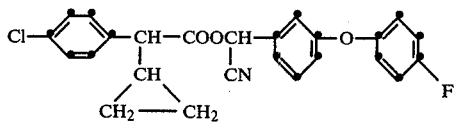

with a refractive index of $n_D^{20} = 1.5880$.

The following compounds are prepared in analogous manner:

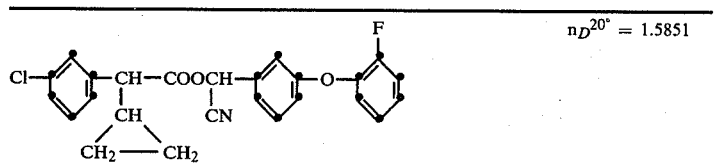

$n_D^{20°} = 1.5851$

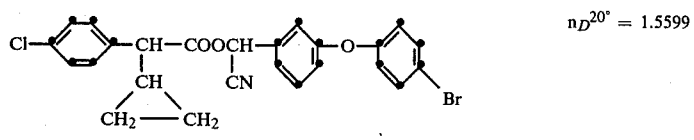

$n_D^{20°} = 1.5599$

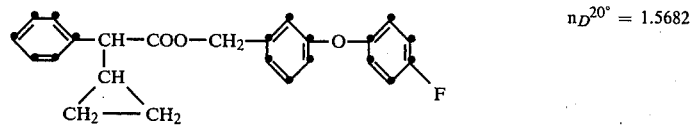

$n_D^{20°} = 1.5682$

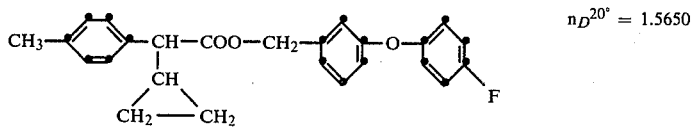

$n_D^{20°} = 1.5650$

-continued
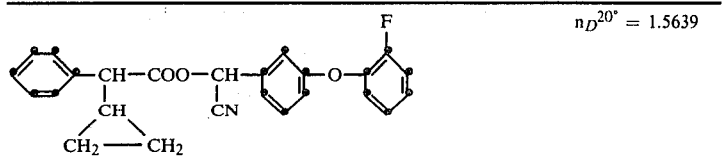 $n_D^{20°} = 1.5639$
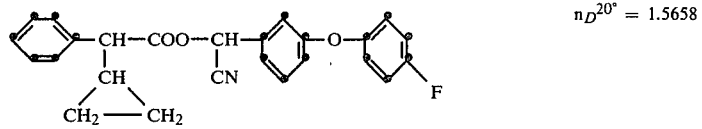 $n_D^{20°} = 1.5658$
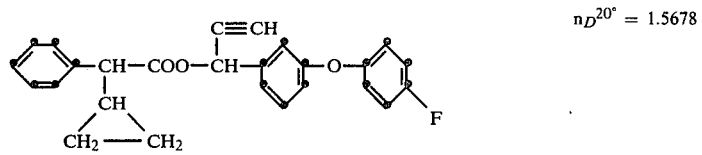 $n_D^{20°} = 1.5678$
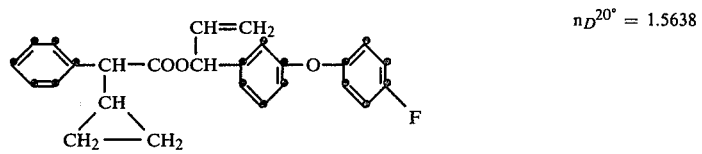 $n_D^{20°} = 1.5638$
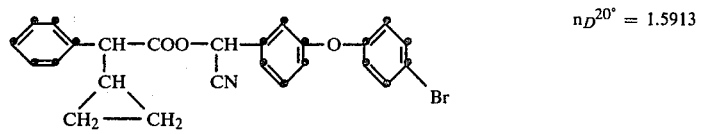 $n_D^{20°} = 1.5913$
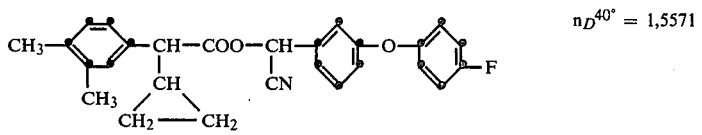 $n_D^{40°} = 1,5571$
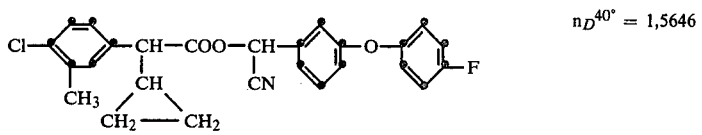 $n_D^{40°} = 1,5646$
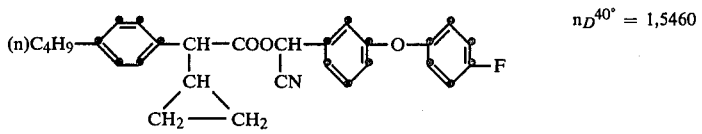 $n_D^{40°} = 1,5460$
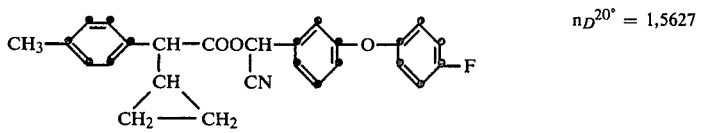 $n_D^{20°} = 1,5627$
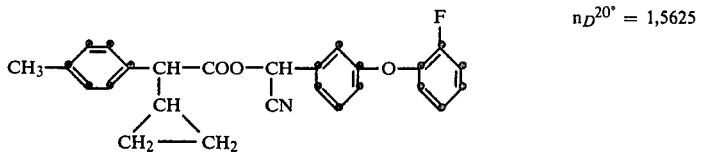 $n_D^{20°} = 1,5625$
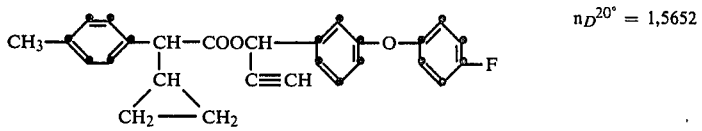 $n_D^{20°} = 1,5652$

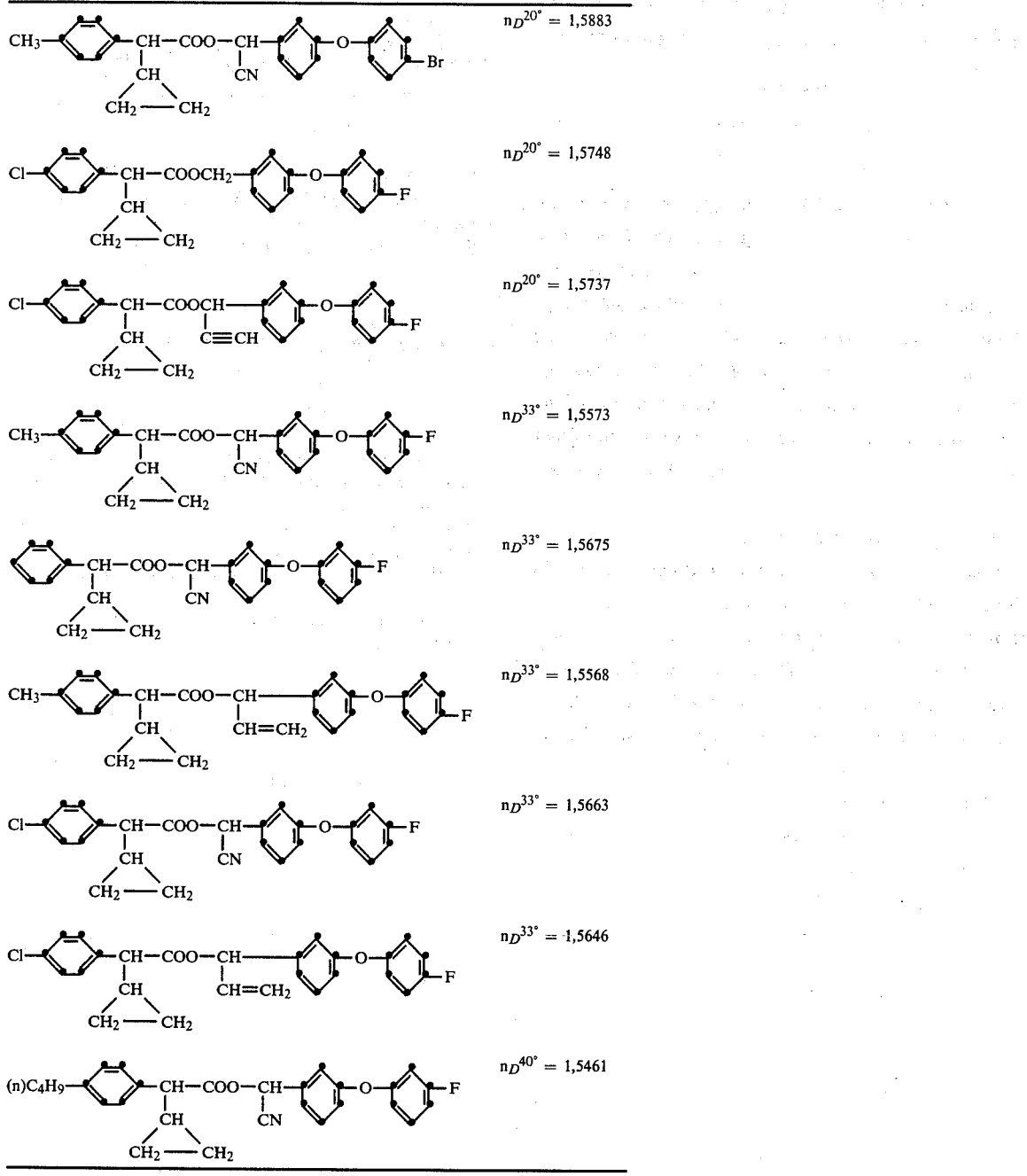

EXAMPLE 2

Insecticidal stomach poison action

Cotton plants were sprayed with a 0.05% aqueous emulsion of active substance (obtained from a 10% emulsifiable concentrate). After the spray coating had dried, the cotton plants were populated with larvae of Spodoptera littoralis and Heliothis virescens in the $L_3$-stage. the test was carried out at 24° C. and 60% relative humidity. In this test, the compounds of Example 1 exhibited a good insecticidal stomach poison action against Spodoptera and Heliothis larvae.

EXAMPLE 3

Acaricidal action

Twelve hours before the test for acaricidal action, Phaseolus vulgaris plants were populated with an infested piece of leaf from a mass culture of Tetranychus urticae. The mobile stages which had migrated to the plants were sprayed with the emulsified test preparations from a chromatography atomiser in such a way that the spray broth did not run off. The number of living and dead larvae, adults and eggs was evaluated under a stereoscopic microscope after 2 and 7 days and the result expressed in percentage values. During the test run, the plants stood in greenhouse compartments at 25° C. In this test, the compounds of Example 1 acted against adults, larvae and eggs of Tetranychus urticae.

EXAMPLE 4

Action against ticks (A) *Rhipicephalus bursa*

Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cottonwool plug and placed on its head to enable the cotton wool to absorb the active substance emulsion. Evaluation of the action against adults was made after 2 weeks and of that against larvae after 2 days. Each test was repeated twice.

(B) *Boophilus microplus* (larvae)

Test were carried out with 20 OP-sensitive and 20 OP-resistant larvae using aqueous emulsions similar to those used in Test A. (The resistance refers to the tolerance towards diazinone). The compounds of Example 1 acted in these tests against adults and larvae of Rhipicephalus bursa and OP-sensitive and OP-resistant larvae of *Boophilus microplus*.

What is claimed is:

1. A compound of the formula

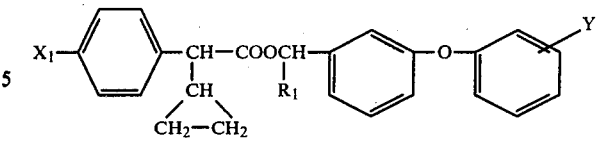

wherein $X_1$ represents chlorine or methyl, $R_1$ represents cyano or or ethynyl, and Y represents o-fluorine or p-fluorine.

2. The compound according to claim 1 of the formula

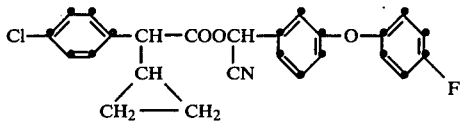

3. A insecticidal and acaricidal composition which contains, as active component, a compound according to claim 1 and suitable carriers.

4. A method for combatting insects and acarids which comprises applying thereto an insecticidally or acaricidally effective amount of a compound according to claim 1.

5. The method according to claim 4 in which the compound is

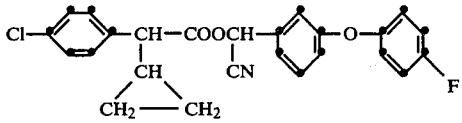

* * * * *